US010138175B2

(12) United States Patent
Tosin et al.

(10) Patent No.: US 10,138,175 B2
(45) Date of Patent: Nov. 27, 2018

(54) PARTICLES INCLUDING ZEOLITE CATALYSTS AND THEIR USE IN OLIGOMERIZATION PROCESSES

(71) Applicant: ExxonMobil Chemical Patents Inc., Baytown, TX (US)

(72) Inventors: Geraldine Tosin, Notre Dame de Gravenchon (FR); Mechilium J. G. Janssen, Kessel-Lo (BE); Paul Hamilton, Eastleigh (GB); Georges M. K. Mathys, Bierbeek (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 247 days.

(21) Appl. No.: 15/096,639

(22) Filed: Apr. 12, 2016

(65) Prior Publication Data

US 2016/0221891 A1 Aug. 4, 2016

Related U.S. Application Data

(62) Division of application No. 13/156,824, filed on Jun. 9, 2011.

(60) Provisional application No. 61/366,704, filed on Jul. 22, 2010.

(30) Foreign Application Priority Data

Sep. 11, 2010 (EP) .................................... 10174865

(51) Int. Cl.
*C07C 2/12* (2006.01)
*C07C 11/02* (2006.01)
*B01J 29/06* (2006.01)
*B01J 29/70* (2006.01)
*B01J 35/02* (2006.01)
*B01J 35/08* (2006.01)
*B01J 37/00* (2006.01)
*C10G 50/00* (2006.01)

(52) U.S. Cl.
CPC ................ *C07C 2/12* (2013.01); *B01J 29/06* (2013.01); *B01J 29/7026* (2013.01); *B01J 35/023* (2013.01); *B01J 35/026* (2013.01); *B01J 35/08* (2013.01); *B01J 37/0009* (2013.01); *B01J 37/0063* (2013.01); *C07C 11/02* (2013.01); *C10G 50/00* (2013.01); *B01J 2229/42* (2013.01); *C07C 2529/40* (2013.01); *C07C 2529/70* (2013.01); *C10G 2300/1081* (2013.01); *C10G 2300/1088* (2013.01); *C10G 2300/1092* (2013.01); *C10G 2300/4018* (2013.01); *C10G 2400/22* (2013.01)

(58) Field of Classification Search
CPC ....... C07C 2/12; C07C 11/02; C07C 2529/70; C07C 2529/40; C10G 2529/70; C10G 2529/40; C10G 2400/22; C10G 2300/4018; C10G 2300/23; C10G 2300/1088; C10G 2300/1092
USPC .......................................... 585/520, 530, 533
See application file for complete search history.

(56) References Cited

U.S. PATENT DOCUMENTS

| | | |
|---|---|---|
| 2,620,314 A | 12/1952 | Hoekstra |
| 3,960,978 A | 6/1976 | Givens et al. |
| 4,016,218 A | 4/1977 | Haag et al. |
| 4,021,502 A | 5/1977 | Plank et al. |
| 4,381,255 A | 4/1983 | Nozemack et al. |
| 4,560,536 A | 12/1985 | Tabak |
| 4,919,896 A | 4/1990 | Harandi et al. |
| 5,183,790 A | 2/1993 | Chitnis et al. |
| 5,397,455 A | 3/1995 | Timken |
| 5,446,222 A | 8/1995 | Boulton et al. |
| 5,464,593 A | 11/1995 | Takahashi et al. |
| 5,558,851 A | 9/1996 | Miller |
| 5,672,800 A | 9/1997 | Mathys et al. |
| 5,962,735 A | 10/1999 | Kulprathipanja et al. |
| 6,143,942 A | 11/2000 | Verrelst et al. |
| 6,403,853 B1 | 6/2002 | Abrevaya et al. |
| 6,517,807 B2 | 2/2003 | Verduijn et al. |
| 6,649,802 B1 * | 11/2003 | Frame .................. B01J 37/0246 585/514 |
| 6,884,914 B2 | 4/2005 | Mathys et al. |
| 7,374,662 B2 | 5/2008 | Duplan et al. |
| 7,501,548 B2 * | 3/2009 | Brown ...................... C07C 2/12 560/98 |
| 7,737,315 B2 * | 6/2010 | Brown ...................... C07C 2/12 560/98 |
| 7,834,229 B2 | 11/2010 | Brown et al. |

(Continued)

FOREIGN PATENT DOCUMENTS

| | | |
|---|---|---|
| EP | 0 220 933 | 5/1987 |
| EP | 746 538 | 12/1996 |

(Continued)

OTHER PUBLICATIONS

Alexander G. Stepanov and Mikhail V. Luzgin, *Interaction of Acetonitrile with Olefins and Alcohols in Zeolite H-ZSM-5: In Situ Solid-State NMR Characterization of the Reaction Products*, Chem. Eur. J., 1997, 3 No. 1, pp. 47-56.

(Continued)

*Primary Examiner* — Elizabeth D Wood
(74) *Attorney, Agent, or Firm* — Darryl M. Tyus (57) ABSTRACT

Embodiments of an invention disclosed herein relate to particles made from zeolite catalysts and their use in oligomerization processes. In particular, shaped particles (for example, spheroid particles) are made from compositions including the contact product of at least one zeolite catalyst and at least one binder.

11 Claims, 4 Drawing Sheets

(56) References Cited

U.S. PATENT DOCUMENTS

| | | | |
|---|---|---|---|
| 8,450,233 B2 | 5/2013 | Nesterenko et al. | |
| 2002/0072467 A1 | 6/2002 | Ogawa | |
| 2003/0113248 A1* | 6/2003 | Mohr | B01J 29/06 |
| | | | 423/213.2 |
| 2003/0149313 A1* | 8/2003 | Murray | C07C 2/12 |
| | | | 568/910 |
| 2004/0006250 A1* | 1/2004 | Mathys | C07C 2/12 |
| | | | 585/17 |
| 2005/0054516 A1 | 3/2005 | Vaughn et al. | |
| 2006/0199987 A1 | 9/2006 | Kuechler et al. | |
| 2006/0224030 A1 | 10/2006 | Euzen et al. | |
| 2007/0213576 A1* | 9/2007 | Brown | C07C 2/12 |
| | | | 585/533 |
| 2008/0188694 A1 | 8/2008 | Schmidt et al. | |
| 2008/0287717 A1* | 11/2008 | Kuechler | C10G 69/126 |
| | | | 585/14 |
| 2009/0118556 A1 | 5/2009 | Euzen et al. | |
| 2009/0134546 A1* | 5/2009 | Brown | C07C 2/12 |
| | | | 264/211 |
| 2009/0216056 A1 | 8/2009 | Beeckman et al. | |
| 2010/0249474 A1* | 9/2010 | Nicholas | B01J 29/7046 |
| | | | 585/330 |
| 2011/0042270 A1 | 2/2011 | Guillon et al. | |

FOREIGN PATENT DOCUMENTS

| | | |
|---|---|---|
| EP | 2 095 866 | 9/2009 |
| GB | 1 418 445 | 12/1975 |
| JP | 2004 238209 | 8/2004 |
| WO | WO1994/12452 | 6/1994 |
| WO | WO2005/118512 | 12/2005 |
| WO | WO2005/118513 | 12/2005 |
| WO | WO2007/006398 | 1/2007 |
| WO | WO2008/088452 | 7/2008 |

OTHER PUBLICATIONS

Bas M. Vogelaar et al., *Analysis of Coke Deposition Profiles in Commercial Spent Hydroprocessing Catalysts Using Raman Spectroscopy*, Fuel 86 (2007), pp. 1122-1129.

\* cited by examiner

PARTICLES INCLUDING ZEOLITE CATALYSTS AND THEIR USE IN OLIGOMERIZATION PROCESSES

CROSS REFERENCE TO RELATED APPLICATIONS

This application is a divisional application of Ser. No. 13/156,824, filed Jun. 9, 2011, that claims the benefit of Serial No. 61/366,704, filed Jul. 22, 2010, and EP 10174865.5, filed Sep. 11, 2010, the disclosures of which are incorporated by reference in their entireties.A1

FIELD OF THE INVENTION

The invention relates to particles comprising zeolite catalysts and their use in to oligomerization processes. In particular, shaped particles (for example, spheres, cylinders, tablets, lobed particles etc.) are made from compositions comprising the contact product of at least one zeolite catalyst and at least one binder. In several classes of embodiments, improvements may be observed in catalyst life, olefin selectivity, and/or coke deposition on the particle during olefin oligomerization.

BACKGROUND OF THE INVENTION

The condensation reaction of an olefin or a mixture of olefins over an acid catalyst to form higher molecular weight products is a widely used commercial process. This type of condensation reaction may be referred to as an oligomerization reaction, and the products are generally low molecular weight oligomers that are formed by the condensation of up to 12, typically 2, 3, or 4, but up to 5, 6, 7, or even 8 olefin molecules with each other. For example, low molecular weight olefins (such as, for example, propene, 2-methylpropene, 1-butene, 2-butenes, pentenes, and hexenes) may be converted by oligomerization processes using zeolite catalysts to a produce oligomers. Exemplary uses of such oligomers include high-octane gasoline blending stocks, starting material for the production of chemical intermediates, and other end-products. Such chemical intermediates and end-products include alcohols, acids, detergents, and esters such as plasticizer esters and synthetic lubricants.

Industrial oligomerization processes employing zeolite catalysts typically run for several weeks before a catalyst change is required or a decommissioning of the reactor is needed. In industrial processes, zeolite catalysts are generally delivered as an extrudate of the zeolite catalyst and a binder. Extrudates may have many shapes and may be distinguished by their shape or number of lobes of each extrudate, for example, cylindrical (solid or hollow), trilobe, quadrulobe, (or simply multilobe).

The feedstocks for the reactions are generally obtained from refining activities such as a stream derived from catalytic or steam cracking that may have been subjected to fractionation. The nature of such refining activities is such that there will be variations in the constituents of the feedstocks. In addition, it may be desirable to change the nature of the feed during a reactor run. Thus, the catalyst activity and the reaction conditions vary according to the composition of the feedstock. As a result, the ideal catalyst provides not only the ability to run a long time as referred to in terms of catalyst life, catalyst activity, or catalyst stability but is also able to oligomerize selectively to produce desired end products using a variety of heterogeneous feedstocks that may contain isomers, poisons, and saturated and unsaturated molecules. Furthermore, the reactions are exothermic and the size of the exotherm also depends upon the nature and amount of the constituents of the feedstock. For example, if isobutylene and propylene are present, they are particularly reactive generating a large amount of heat of reaction.

The high temperatures generated may lead to carbonaceous deposits on the catalyst caused by a build up of condensed, heavy hydrocarbons similar to asphalt. Such deposits are commonly termed "coke" and lead to deactivation of the zeolite catalyst. In general, the higher the concentration of olefin in the feed, the higher will be the rate of heat release from the catalyzed reaction, and thus, the higher the temperatures reached. Consequently, there will be a higher rate of coke formation and deposition of coke on the catalyst particle. As a result, this has placed a limit on the maximum concentration of olefin that can be tolerated in the feed.

Useful feed streams containing olefins such as $C_3$ and $C_4$ olefins may be refinery streams derived from steam cracking or catalytic cracking and the composition of the stream will depend upon the raw material from which it is produced and the production technology employed. For example, propylene refinery streams may typically contain up to 75 wt % propylene with the balance being predominantly propane. Similarly butene refinery streams may typically contain up to 70 wt % butenes with the balance being predominantly butanes. Poisons, such as, for example, nitrogen containing compounds (e.g., nitrites) and sulfur containing compounds, and isomeric equivalents are also most likely present. Thus, the reactivity of the olefins in oligomerization processes with zeolite catalysts varies according to the nature of the olefin, its concentration in the feedstock, and other variable constituents.

Background references include U.S. Pat. Nos. 3,960,978, 4,016,218, 4,021,502 4,381,255, 4,560,536, 4,919,896, 5,446,222, 5,464,593, 5,672,800, 6,143,942, 6,403,853, 6,517,807, 6,884,914, 7,374,662, U.S. Patent Application Publication Nos. 2005/0054516, 2006/0199987, 2009/0216056, EP 0 220 933 A. EP 746 538 A, EP 2 095 866 A, WO 1994/12452, WO 2005/118512, WO 2005/118513, WO 2007/006398, WO 2008/088452, GB 1 418 445 A, JP 2004 238209 A, *Interaction of Acetonitrile with Olefins and Alcohols in Zeolite H-ZSM-5: In Situ Solid-State NMR Characterization of the Reaction Products*, Alexander G. Stepanov, Mikhail V. Luzgin, Chem. Eur. J., 1997, 3, No. 1, pp. 47-56, and *Analysis of Coke Deposition Profiles in Commercial Spent Hydroprocessing Catalysts Using Raman Spectroscopy*, Bas M. Vogelaar et al. Fuel 86 (2007), pp. 1122-1129.

Therefore, there remains a need for improvements in particles comprising zeolite catalysts that provide for extended production runs yielding desired end products. Additionally, there remains a need for the particles to be able to oligomerize in presence of higher concentrations of catalyst poisons and yet yield higher concentrations of the desired end product. It will be appreciated that in large scale industrial processes, small increases in production (such as ≥1%) have highly significant value.

SUMMARY OF THE INVENTION

In a class of embodiments, the invention provides for a particle made from a composition comprising the contact product of: (1) at least one zeolite catalyst; and (2) at least one binder; wherein the particle is a spheroid particle. The particle may be utilized in a process for the oligomerization of $C_3$-$C_{15}$ olefins.

In any of the embodiments described herein, the at least one zeolite catalyst may be selected from one or more family members belonging to a TON structure, MFI structure, MFS structure, MWW structure, and mixtures thereof.

In any of the embodiments described herein, the at least one zeolite catalyst may be selected from at least one of ZSM-5, ZSM-22, ZSM-57, MCM-22, MCM-48, and mixtures thereof.

In any of the embodiments described herein, the spheroid particle may have an average particle size of from 0.1 mm to 5.0 mm (BS 1796-1: 1989).

In any of the embodiments described herein, the spheroid particle may have an average particle size of from 0.1 mm to 4.0 mm (BS 1796-1: 1989).

In any of the embodiments described herein, the spheroid particle may have average particle size of from 0.3 mm to 3.0 mm (BS 1796-1: 1989).

In any of the embodiments described herein, the spheroid particle average particle size of from 0.5 mm to 1.5 mm (BS 1796-1: 1989).

In any of the embodiments described herein, the composition may comprise from 25 to 99 wt % of the at least one zeolite catalyst based upon the total weight of the composition.

In any of the embodiments described herein, the composition may comprise from 45 to 80 wt % of the at least one zeolite catalyst based upon the total weight of the composition.

In any of the embodiments described herein, the composition may comprise from 50 to 75 wt % of the at least one zeolite catalyst based upon the total weight of the composition.

In another class of embodiments, the invention provides for a process for producing the spheroid particle comprising producing the spheroid particle by the spherical granulation of the composition by a vibrational dropping process.

In yet another class of embodiments, the invention provides for a process for producing the spheroid particle by a spheronization process.

And yet in another class of embodiments, the invention provides for a process for the oligomerization of olefins, the process comprising: contacting at least one spheroid particle under oligomerization conditions with a feedstock comprising at least one $C_3$-$C_{15}$ olefin or a mixture thereof to form at least one oligomer product.

DETAILED DESCRIPTION

Before the present compounds, components, compositions, and/or methods are disclosed and described, it is to be understood that unless otherwise indicated this invention is not limited to specific compounds, components, compositions, reactants, reaction conditions, structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified.

Oligomerization processes described herein employ spheroid particles made from a composition comprising the contact product of at least one zeolite catalyst and at least one binder. The composition may include or be made with optional processing aids or other optional components. Embodiments of inventive processes may exhibit improved catalyst life and/or improved olefin selectivity that result in higher oligomer yield, and/or the ability to oligomerize in the presence of higher catalyst poisons or contaminants.

Zeolite Catalysts

The catalysts utilized in the oligomerization processes of embodiments of the invention, i.e., at least one zeolite catalyst, may be any suitable zeolite catalyst(s) capable of oligomerizing olefins. Zeolites are the aluminosilicate members of the family of microporous solids known as "molecular sieves." The term molecular sieve refers to a particular property of these materials, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon or aluminum atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites may not be cylindrical.

In an embodiment, the at least one zeolite catalyst may include a medium pore size molecular sieve having a Constraint Index of about 1 to about 12. Constraint Index and a method of its determination are described in, for example, U.S. Pat. No. 4,016,218.

Examples of the at least one zeolite catalyst include those of the TON structure type (for example, ZSM-22, ISI-1, Theta-1, Nu-10, and KZ-2), those of the MTT structure type (for example. ZSM-23 and KZ-1), those of the MFI structure type (for example, ZSM-5), those of the MFS structure type (for example, ZSM-57), those of the MEL-structure type (for example, ZSM-11), those of the MTW structure type (for example, ZSM-12), those of the EUO structure type (for example, EU-1), those of the AEL structure type (for example, SAPO-11), members of the ferrierite family (for example, ZSM-35) and members of the ZSM-48 family of molecular sieves (for example, ZSM-48). Other examples include MWW (e.g., MCM-22, MCM-48), MOR, or beta type catalysts. As used herein, the term "structure type" is used as described in the Structure Type Atlas, Zeolites 17, 1996.

In an embodiment, the at least one zeolite catalyst is selected from at least one of ZSM-5, ZSM-11, ZSM-12, ZSM-18, ZSM-22, ZSM-23, ZSM-35, ZSM-38, ZSM-48, ZSM-50, ZSM-57, and mixtures thereof.

In a class of embodiments, the at least one zeolite catalyst comprises molecular sieves having pores formed by 10-membered rings of tetrahedrally coordinated atoms, such as molecular sieves having the TON or MFS structure type.

Mixtures of two or more of catalysts may be used in the processes. For example, the mixture may include ZSM-22 and ZSM-57 or ZSM-22 and ZSM-5 or ZSM-57 and ZSM-5. The at least one zeolite catalyst may also be combined with other catalysts such as a solid phosphoric acid (sPa) catalyst.

In a class of embodiments, the at least one zeolite catalyst is used in its H- or acid form.

The at least one zeolite catalyst may have an average crystallite or particle size of up to 15 µm, such as within the range of from 0.01 to 6 µm, alternatively, from 0.05 to 5 µm, and alternatively, from 0.1 to 3 µm. As used herein, "average particle size" refers to the arithmetic average of the diameter distribution of the crystals on a volume basis.

In several embodiments, an as-synthesized molecular sieve is advantageously converted to its acid form, for example, by acid treatment, e.g., by HCl, acetic acid, etc., or by ion exchange, for example, ammonium ion exchange. Subsequently, it may undergo calcination before use. The calcined materials may be post-treated, such as by steaming.

For example, the at least one zeolite catalyst may be produced by any suitable method. One technique includes heating a reaction mixture containing a source of silicon oxide, a source of aluminum oxide and, if appropriate, an organic promoter, for example, a nitrogen or phosphorus-containing organic base, together optionally, with an alkali metal base, and separating the porous aluminosilicate crystals (zeolite precursor crystals) formed. The precursor crystals are then calcined in air or oxygen at a temperature exceeding or about 500° C., for example, at a temperature of 550° C. for about 10 to about 20 hours. As recognized in the art, calcination temperatures and durations may vary depending on the type of zeolite catalyst or combination of zeolite catalysts selected. In one embodiment, the calcined material is exchanged with ammonium ions (NH4+) and subjected to conditions under which the ammonium ions decompose, with the formation of ammonia and a proton, thus, producing an acidic form of the at least one zeolite catalyst. Alternatively, the acidic form of the catalyst may be obtained by acid exchange with hydrochloric acid, acetic acid, etc. If desired, however, the calcined material may be used as a catalyst without first being exchanged with ammonium ions, since the material already possesses acidic sites.

Ammonium exchanged and calcined monodimensional 10-rings zeolites (e.g., ZSM-22 and ZSM-23) may be treated to selectivate their surface, thereby, forming a selectivated catalyst. This selectivation may be achieved in numerous ways. In an embodiment, the at least one zeolite catalyst may be titrated with an organic nitrogen base, such as collidine. See, for example, U.S. Pat. No 5,026,933. Another example is by depositing a crystalline Si:Al layer on a core of zeolite where this layer has a higher Si:Al ratio than the untreated zeolite. See, for example, U.S. Pat. No. 6,013,851.

Although much of the discussion above is directed to aluminosilicate zeolites, it is possible to use material in which silicon and aluminum have been replaced in whole or in part by other elements, for example, any one or more of a Group 2 to Group 15 atom. For example, silicon may be replaced by or contacted with germanium and aluminum or may be replaced with boron, gallium, chromium, and iron, As used herein, these materials containing is such replacement lattice elements may also be termed zeolites.

Exemplary catalyst materials and processes for making and using may also be found in U.S. Pat. Nos. 3,960,978, 4,016,218, 4,021,502, 4,381,255, 4,560,536, 4,919,896, 5,446,222, 5,672,800, 6,143,942, 6,517,807, 6,884,914, U.S. Patent Application Publication No. 2006/0199987, EP 746 538 A, WO 1994/12452, WO 2005/118512, WO 2005/118513, WO 2007/006398, and WO 2008/088452. See also "Atlas of Zeolite Structure Types," Eds. W. H. Meier, D. H. Olson and Ch, Baerlocher, Elsevier, Fourth Edition, 1996.

Binders

The at least one zeolite catalyst may be contacted with at least one binder to form a composition that may be formed into a spheroid particle discussed in more detail below. The at least one binder may be a metal oxide and/or a clay. Suitable exemplary binder materials include at least one of alumina, silica, an aluminosilicate, clay, and mixtures thereof. In an embodiment, the binder is aluminum oxide ($Al_2O_3$) or commonly referred to as alumina.

For example, in an embodiment, the composition to be fashioned into a spheroid particle may comprise alumina and ZSM-22 or the composition may comprise alumina and ZSM-57.

In a class of embodiments, the composition to be fashioned into a spheroid particle may comprise from 10:90 to 90:10, alternatively, from 20:80 to 80:20, of the at least zeolite catalyst to the at least one binder by weight.

In an alternative class of embodiments, the composition may comprise from 1 to 99 wt % of the at least one zeolite catalyst based upon the total weight of the composition, alternatively, from 20 to 80 wt % of the at least one zeolite catalyst based upon the total weight of the composition, alternatively, from 25 to 75 wt % of the at least one zeolite catalyst based upon the total weight of the composition, alternatively, from 30 to 75 wt % of the at least one zeolite catalyst based upon the total weight of the composition, and alternatively, from 40 to 7.5 wt % of the at least one zeolite catalyst based upon the total weight of the composition. The remainder of the composition may be or comprise of one or more binders and/or one or more other additives or processing aids.

The composition may be produced through any method known in the art. Mixing may be performed with conventional methods and equipment. In some embodiments, mixing may be performed in the presence of solvents or water.

Other Components and Processing Aids

The composition to be formed into a spheroid particle may be mixed or contacted with at least one processing aid and/or comprise other components. Processing aids help the mixing, mulling, and extruding operation, and may improve the mechanical and/or physical properties of the composition or resulting particle. For example, a processing aid may promote bridging of inorganic particles during the kneading, molding, drying, and calcination, and/or ensure the mechanical stability of the composition. The processing aids may also help disperse solvents, if used, more homogeneously throughout the composition. Processing aids are usually removed during calcination. When a metal carboxylate is used as a processing aid, the metal (e.g., its oxide) is generally incorporated into the composition during calcination.

The composition may comprise other components, including, for example, amines, alkyl amines, carboxylic acids, alkyl ammonium compounds, amino alcohols, cellulose, cellulose ethers, fillers, starch, polyacrylates, polymethacrylates, polyvinyl alcohols, poly(vinylpyrrolidone)s, poly(amino acid)s, polyethers, poly(tetrahydrofuran)s, metal carboxylates, and mixtures thereof.

Examples of cellulose ethers include sodium carboxymethylcellulose, hydroxyethylcellulose, methylcellulose, and derivatives thereof. Examples of poly(alkylene oxide)s are polyethylene oxides, poly(propylene oxide)s, or copolymers of ethylene oxide and propylene oxide.

In some embodiments, the composition to be shaped into a spheroid particle may include one ore more emulsifiers and/or one or more materials described above to modify the properties of the particle.

Spheroidal Particles

The composition comprising the contact product of the at least one zeolite catalyst and the at least one binder may formed into a spheroid particle by any process that is capable of producing a spheroid structure from the compositions described above. As used herein, "spheroid particle" may refer to any ellipsoid structure. AS used herein, "ellipsoid" may be described as an ellipse that has been rotated about at least one of its axis. In a class of to embodiments, the spheroid particle may have two equal semi-diameters. The spheroid particle may be one or more of a prolated spheroid (elongated), oblate spheroid (flattened), and sphere itself. As used herein, "spheroid particle" may also refer to two or three dimensional ovoid particles, for example, an ovum (egg). As used herein, "particle(s)" refers to discrete units of material structure as discussed in Hawley's Condensed Chemical Dictionary, Richard J. Lewis Sr., 13$^{th}$ ed., 1997, John Wiley & Sons, Inc., page 840. For the sake of brevity, when spheroid particle is used it may refer to any definition as defined herein as well as refer to one or more of the spheroid particles defined herein. In a class of embodiments, the spheroid particle is not a cylinder. In another class of embodiment, the spheroid particle is not an extrudate. In a class of embodiments, the spheroid particle is not produced using a spray-dried method.

in a class of embodiments, the spheroid particle may be produced by the spherical granulation of a composition by a vibrational dropping process. This technology is commercially available from Brace GMbH, Alzenau, Germany. In general, the technology introduces a liquefied composition through a vibrating nozzle system wherein the exiting stream breaks up into uniform droplets. When dropped or released from the system, the surface tension of the droplets shapes them into a spheroid. Following, the droplets undergo a solidification step. Solidification may be achieved in a gaseous medium through cooling, drying, and/or in liquid medium. The resulting materials are spheroid particles.

In another class of embodiments, the spheroid particle may be produced by a spheronization process. One such process or technology is known as the MARUMERIZER™ process (developed by Fuji Paudal of Osaka, Japan) and is available from LCI Corp., Charlotte, N.C. In general, the process involves the formation of marumes or spheronizing noodles of a given composition. The composition is then fed into a MARUMIZER apparatus which operates by centrifugal force on the noodles to form them into spheronized particles or spheroid particles.

See also WO 97/22680, WO 02124755, EP 0 046 535 A. EP 2 095 866 A, GB 1 418 445 A, U.S. Pat. Nos. 3,277,520, 3,584,334, 3,741,703, 3,743,464, 5,464,593, 6,923,984, and U.S. Patent Application Publication No. 2005/0054516 for more information and details as to how to produce spheroid particles under several embodiments of the invention.

In several embodiments, the spheroid particles may exhibit one or more of the following properties: free flowing, comprise embedded agents, have high porosity, have to precise fitting diameters, carry a coating, have a high density, and be activated/doped.

As used herein, "average particle size" with reference to the spheroid particle refers to the arithmetic average of the diameter distribution of the spheroid particles. The spheroid particle may have an average particle size of at least about or from 0.1 mm, 0.2 mm, 0.3 mm, 0.4 mm, or 0.5 mm up to and including 1.0 mm, 1.5 mm, 2.0 mm, 2.5 nun. 3.0 mm. 4.0 mm, or 5.0 mm, including any range disclosed therein. Methods of measuring the spheroid particle are known and any suitable method may be used. Examples include electron microscopy or sieving using a mesh size in accordance with ASTM 16, Methods of measurement and definitions of particle diameters are presented in Table 2.1 of Powder Sample and Particle Size Determination by Terence Allen, 2003, Elsevier Science and Technology Books, ISBN 9780444515643, and are applied herein. In a class of embodiments, a sieving method is applied including using one or more mesh screens to concentrate particles having particular average particle sizes. A preferred method of measurement is provided in British Standard (BS) 1796-1: 1989 cross-referenced as ISO 2591-1: 1988. This method is applied unless otherwise stated given its ease and convenience on a commercial scale to quickly concentrate a large volume of particles having a particular average particle size.

In several classes of embodiments, the spheroid particles may exhibit improved bulk densities as compared to conventional catalyst particles. For example, spheroid particles may have may have a bulk density 0.50 gram/cc or more, alternatively, a bulk density of 0.55 gram/cc or more, alternatively, a bulk density of 0.60 gram/cc or more, and alternatively, a bulk density of 0.65 gram/cc or more. Bulk densities are important features of these embodiments because the bulk densities as describe above provide for more mass of catalyst per reactor volume resulting in higher product yields.

In other classes of embodiments, hexane uptake may be used to measure the available micro-pore volume of the catalyst particles. For example, the spheroid particle may exhibit a hexane uptake of 40 mg hexane/gram catalyst or more, alternatively, a hexane uptake of 45 mg hexane/gram catalyst or more, alternatively, a hexane uptake of 50 mg hexane/gram catalyst or more, and alternatively, a hexane uptake of 55 mg hexane/gram catalyst or more.

In another class of embodiments, the bulk crush strength may be used to measure the resistance to fracturing of the catalyst particles. For example, the spheroid particle may have a bulk crush strength according to ASTM D7048 of 15 psig or more, alternatively, 20 psig or more, alternatively, 25 psig or more, and alternatively, 30 psig or more. These are important characteristics when loading and unloading catalyst particles into and out of a reactor.

In a class of embodiments, for a given population of spheroid particles, not all members need to be uniform and the given population may comprise non-uniform members in shape taking into account irregularities that may result in the manufacturing process, handling/transport, defects that develop during use or regeneration, contaminants, etc. As used herein, "uniform" refers to having the same form. In general classes of embodiments, a given class of spheroid particles comprises 30% or more uniform members, alternatively, 40% or more uniform members, alternatively, 50% or more uniform members, alternatively, 60% or more uniform members, alternatively, 70% or more uniform me alternatively, 80% or more uniform members, and, alternatively. 90% or more uniform members, based upon the total given population.

Feedstocks and Oligomerization

The feedstock typically comprises olefins having from about 2 to about 15 carbon atoms, such as, for example, from about 2 to about 6 carbon atoms. Additionally, in several embodiments, the feedstock may comprise an oligomer, such as, for example, a dimer, especially one provided by recycling a part of a product stream.

in class of embodiments, the feedstock comprises one or more of propene, butenes, pentenes, hexenes, their isomers, and mixtures thereof. The process is especially useful for the oligomerization of feedstocks comprising propene, butenes, other components, and mixtures thereof.

As used herein, "oligomer(s)" or "oligomer product" refers to a polymer molecule (or a mixture of polymer molecules) made from a few monomer units such as, for example, a dimer, a trimer, a tetramer, a mixture thereof, etc. In a class of embodiments, "oligomer(s)" refers to a polymer molecule (or a mixture of polymer molecules) having 20 carbon atoms or less, alternatively, 15 carbon atoms or less, alternatively, 10 carbon atoms or less, alternatively, 9 carbon atoms or less, and alternatively, 8 carbon atoms or less. As used herein, "oligomerization process" refers to any process of catalytically joining monomer units to form the oligomer(s) as defined above. In a class of embodiments, oligomerization process is used synonymously with "polymerization process." As used herein, the term "oligomerization conditions" refers to any and all those variations of equipment, conditions (e.g. temperatures, pressures, etc.), materials, and reactor schemes that are suitable to conduct the oligomerization process to produce the oligomer(s) as known and applied in the to art and discussed more below.

In an embodiment, the oligomerization process may consist essentially of one or more single-step oligomerization processes.

In a class of embodiments, the feedstock may contain 30 wt % or more olefins, alternatively, 40 wt % or more olefins, alternatively, 50 wt % or more olefins, alternatively, 60 wt % or more olefins, alternatively, 70 wt % or more olefins, and alternatively, 80 wt % or more olefins, based upon the total weight of the feed. The olefins to be oligomerized may be one or more of $C_3$-$C_{15}$ olefins or mixtures thereof, alternatively, $C_3$-$C_6$ olefins or mixtures thereof, and alternatively. $C_3$-$C_5$ olefins or mixtures thereof.

The feedstock may also comprise other hydrocarbons such as, for example, at least one saturated hydrocarbon (e.g., at least one alkane) having the same or different number of carbon atoms as the olefin(s) in the feedstock.

Additionally, the feedstock may comprise isomers of any of the constituents found therein. As used herein, "isomer" refers to compounds having the same molecular formula but different structural formula. Examples may be structural isomers, stereoisomers, enantiomers, geometrical isomers, etc. Typically, the feedstock may comprise at least one isomer of the olefin(s) in the feedstock.

In a class of embodiments, the feedstock may also comprise contaminants or compounds that may hinder catalyst life or productivity. These may include nitrogen, sulfur, chlorine, or compounds incorporating the aforementioned elements, and mixtures thereof. Ethers such as di-isopropylether (DIPE) may also be a contaminant that may be removed from the feedstock.

Examples of nitrogen containing compounds include acetonitrile, ammonia, amines, propionitriles and mixtures thereof. Examples of sulphur containing compounds include mercaptans such as, for example, methyl mercaptan, ethyl mercaptan, propyl mercaptan, dimethyl sulfide, diethyl sulfide, ethyl methyl sulfide, n-propyl sulfide, 1-propane thiol, 2-propane thiol, 1-butane thiol, 1,1-methylethyl thiol, ethylmethyl disulfide, dimethyl disulfide, tetrahydrothiopene, and mixtures thereof.

Examples of suitable feedstocks include untreated refinery streams such as Fluidized Catalytic Cracking (FCC), coker, and pytms streams as well as aromatics-containing streams, such as, for example, reformates.

Other examples include Raffinate-1 (RAF-1) and/or Raffinate-2 (RAF-2). Typically, Raffinate-1 and Raffinate-2 may be regarded as stages in the processing of crude, generally, $C_4$ streams. These streams are usually from olefin steam crackers but may also to come from refinery cat-crackers in which case they generally contain the same components but in different proportions. The first stage of the process is to remove, by generally solvent extraction or hydrogenation, the butadiene which may be 40-45% of the stream. The remaining product is Raffinate-1. It generally consists of isobutylene, the two normal isomers, butene-1 and butene-2, and smaller quantities of butanes and other compounds. Removal of the isobutylene, usually by reaction with methanol to produce MTBE, leaves Raffinate-2. Raffinate 3 (RAF-3) is less common but may also be used. Raffinate 3 may be obtained after separation of 1-butene from Raffinate 2 with a residual 1-butene content of about 1%.

In another embodiment, the feedstock comprises an FCC light olefin stream that typically comprises ethane, ethylene, propane, propylene, isobutane, n-butane, butenes, pentanes, and other optional components. A specific example of such a feedstock may comprise the following:

|  | Wt % | Mol % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

In several classes of embodiments the feedstock may comprise a diluent. The diluent may comprise any suitable hydrocarbon such as alkanes. The alkanes may be represented the general formula: $C_nH_{2n+2}$, wherein n is a number from 1 to 20, alternatively, from 1 to 10, alternatively, from 1 to 5, and alternatively, from 3 to 4. Examples may include methane, ethane, propane, butane, pentane, and mixtures thereof. In a class of embodiments and when the diluent is present, the feedstock may comprise at least 10%, at least 25%, at least 30%, at least 35%, or at least 40% of the diluent, for example, the alkane such as propane and/or butane, based upon the total volume of the feedstock. Alternatively stated, the diluent may be present in the feedstock in the range from 10% to 40%, alternatively, from 10% to 35%, and alternatively, from 20% to 35% based upon the total volume of the feedstock. The diluent may also be delivered to the reactor(s) through separate feedstreams. to When fed separately, the diluent may be fed in amounts to be equivalent to the embodiments wherein the diluent is co-fed with the feedstock. These amounts may not necessarily be the same as the ranges stated above given that more or less of the diluent may necessary when fed separately to provide an equivalent.

Additionally, the feedstock may undergo further processing and purification steps prior to being introduced in the oligomerization reactor(s).

In several classes of embodiments and prior to oligomerization, the feedstock may be hydrated. (i.e., contacted with water) and in an embodiment sufficient water may be added to saturate the feedstock. In particular, the feedstock may comprise from about 0.01 to about 0.25, alternatively, from about 0.02 to about 0.20, and alternatively, from about 0.03 to about 0.10, mol % water based on the total hydrocarbon content of the feedstock. If desired and by way of example, the water content of the feedstock may be increased by passage through a thermostatted water saturator.

The reaction system may include one or more of a fixed bed reactor, a packed bed reactor, a tubular reactor, a fluidized bed reactor, a slurry reactor, and/or a continuous catalyst regeneration reactor. They may be operated in any combination such as, for example, in series and/or parallel sequence. In several embodiments, they may be operated in continuous or batch mode.

The oligomerization conditions may include operating temperatures from about 80° C. to about 350° C. Close to and above the upper end of the range, deoligomerization rates increase and may predominate over the oligomerization reaction providing an upper limit to practical operation. More typically, the reaction temperature is from about 130° C. to about 320° C., alternatively, from about 135° C. to about 310° C., and alternatively, from about 160° C. to about 270° C.

The pressure may be in the range of from about 400 psig to about 4000 psig (2860 to 27680 kPa), and alternatively, from about 500 psig to about 1500 psig (3550 to 10440 kPa).

The olefin weight hourly space velocity may be in the range of from about 0.1 hr$^{-1}$ to about 20 hr$^{-1}$ or from about 0.5 hr$^{-1}$ to about 5 hr$^{-1}$.

In one embodiment, process is conducted at a temperature of 80-350° C.; an olefin weight hourly space velocity of 0.1-20 hr$^{-1}$; and a pressure of 2860-27680 kPa.

In another embodiment, the process is conducted at a temperature of 130-320° C.; an olefin weight hourly space velocity of 0.5-5 hr$^{-1}$; and a pressure of 3550-1044 kPa.

In a class of embodiments, the oligomer product may include a hydrocarbon composition comprising at least 80 wt %, alternatively, at least 90 wt % based upon the total weight of the reactor effluent (the final reactor effluent if one or more reactors are utilized) of $C_8$ to $C_{20}$ olefin or a mixture thereof.

The oligomer product is useful in many applications and is the starting material for further processes. For example, the oligomer product may be polymerized to produce polyolefins that have application in the plastic industry and synthetic basestocks for lubricants. The oligomer product may undergo hydroformylation and subsequently hydrogenation to produce alcohols. The alcohols may be used in industry such as, for example, solvents. The alcohols may further be used in many other areas of industry such as, for example, undergoing esterification to produce esters that have application as plasticizers.

Catalyst Life

As used herein, "catalyst life" (Tpdt/Tcat) describes the number of tons of product produced per ton of formulated catalyst. It may be plotted against a setpoint temperature at a given space velocity and at a given olefin conversion rate. For example, a plot may provide a comparison between oligomerization processes using spheroid particles and extrudates (for example, $\frac{1}{16}^{th}$ inch (1.5875 mm) and $\frac{1}{20}^{th}$ inch (1.2700 mm) quadrulobe extrudates).

In a class of embodiments, the spheroid particles provide for a longer catalyst life (for example, as represented by Tpdt/Tcat) at a desirable conversion. For example, these embodiments may enjoy an increase in catalyst life as compared to extrudates of the same chemical composition, of 10% or greater, alternatively, 20% or greater, alternatively, 30% or greater, alternatively, 40% or greater, alternatively, 50% or greater, alternatively, 75% or greater, alternatively, 100% or greater, alternatively, 150% or greater, and alternatively, 200% or greater, at oligomerization temperatures of from 180° C. to 320° C., alternatively, 210° C. to 300° C., alternatively, 210° C. to 250° C., and alternatively, 210° C. to 240° C., at an olefin constant conversion rate of from 60 to 99 wt % based upon the total weight of olefins, alternatively, from 70 to 95 wt %, alternatively, from 75 to 99 wt %, alternatively, from 75 to 95 wt %, and alternatively, at about 75 wt %. The space velocity for the aforementioned embodiments may be in the range of 1 to 20 h$^{-1}$. In an embodiment, the space velocity is 12 h$^{-1}$.

In another class of embodiments, the spheroid particles provide for a longer catalyst life and at desirable olefin conversion rates. For example, these embodiments may enjoy an increase in catalyst life of from 2750 Tpdt/Tcat or greater, alternatively, 3000 Tpdt/Tcat or greater, alternatively, 3100 Tpdt/Tcat or greater, alternatively, 3500 Tpdt/Tcat. or greater, alternatively, 4000 Tpdt/Tcat or greater, alternatively, 5000 Tpdt/Tcat or greater, alternatively, 6000 Tpdt/Tcat or greater, alternatively, 7000 Tpdt/Tcat or greater, and alternatively, 8000 Tpdt/Tcat or greater, (alternatively stated, from any one of the aforementioned numerical values to 25,000 Tpdt/Tcat to provide a closed numerical range) at oligomerization temperatures from 180° C. to 320° C., alternatively, 210° C. to 300° C., alternatively, 210° C. to 250° C., and alternatively, 210° C. to 240° C., at an olefin constant conversion rate of from 60 to 99 wt % based upon the total weight of olefins, alternatively, from 70 to 95 wt %, alternatively, from 75 to 99 wt %, alternatively, from 75 to 95 wt %, and alternatively, at about 75 wt %. The space velocity for the aforementioned embodiments may be any one of 1, 2, 4, 6, 8, 10, 12, 14, 16, 18, 20 h$^{-1}$. In an embodiment, the space velocity is 12 h$^{-1}$.

Olefin Selectivity

Embodiments described herein may exhibit improvements in olefin selectivity at given conversion rates that result in higher oligomer yield. Olefin selectivity may be defined as the weight of olefins having a given carbon number divided by the total weight of the product. For example, olefin selectivities may increase by 1 wt % or greater, alternatively, 2 wt % or greater, 3 wt % or greater, alternatively, 4 wt % or greater, alternatively, 5 wt % or greater, alternatively, 6 wt % or greater, alternatively, 7 wt % or greater, alternatively, 8 wt % or greater, alternatively, 9 wt % or greater, and alternatively, 10 wt % or greater, based upon the total weight of the product at an olefin constant conversion rate of from 60 to 99 wt % based upon the total weight of olefins in feed, alternatively, from 70 to 95 wt %, alternatively, from 75 to 99 wt %, alternatively, from 75 to 95 wt %, and alternatively, at about 75 wt %, and at oligomerization temperatures from 180° C. to 320° C., alternatively, 210° C. to 300° C., alternatively, 210° C. to 250° C., and alternatively, 210° C. to 240° C. The space velocity for the aforementioned embodiments may be any one of 1, 2, 4, 6, 8, 10, 12, 14, 16, 18, 20 h$^{-1}$. In an embodiment, the space velocity is 12 h$^{-1}$. In several classes of embodiments, olefin selectivity may directed to the production of $C_6$-$C_{16}$ oligomers or mixtures thereof from $C_3$-$C_6$ feedstocks or mixtures thereof, alternatively, $C_7$-$C_8$-$C_9$ oligomers or mixtures thereof from $C_3$-$C_4$ feedstocks or mixtures thereof.

Coke Deposition

Embodiments described herein may exhibit improvements in coke deposition, especially during longer oligomerization process runs, as compared to extrudates. As previously explained, high temperatures generated may lead to carbonaceous deposits on the catalyst caused by a build up of condensed, heavy hydrocarbons similar to asphalt. Such deposits are commonly termed "coke" and lead to deactivation of the catalyst. In general, the higher the concentration of olefin in the feed, the higher will be the rate of heat release from the catalyzed reaction, and thus, the higher the temperatures reached. Additionally, the oligomerization temperature is typically increased When catalyst activity begins to decrease. Consequently, there will be a higher rate of coke formation when measured at the end of the reactor run. In embodiments disclosed herein, coke deposition may be much less than that of processes using extrudates. For example, coke deposition for inventive spheroid particles and their corresponding oligomerization processes may be 15 wt % or less, alternatively, 9 wt % or less, alternatively, 8 wt % or less, alternatively, 7 wt % or less, alternatively, 6 wt % or less, based upon the total weight of the catalyst. Without being bound to theory, the improvements associated with the reduction of coke deposition on the catalyst particle may be at least partially responsible for or related to the improvements in longer catalyst life and/or olefin selectivity.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description and are not intended to limit the scope of that which the inventors regard as their invention.

Olefin oligomerizations were conducted at different space velocities utilizing butene and propylene feeds. The butene runs ran at space velocities of 2, 6, 12 or 18 $h^{-1}$ and the propylene runs ran at space velocities of 1, 2, 4, 6 and 12 $h^{-1}$ over a range of conversion levels of 70 to 90% for butene and 90 to 96% for propylene. For these runs, the reaction temperature was adjusted to maintain the target conversion. As the catalyst deactivated, the reaction temperature was raised as shown in the figures. This process is monitored by plotting the temperature to achieve target conversion at a given WHSV against time. It is desirable to track the stability of catalyst between and within individual runs by using different feed rates. Therefore, the time was replaced by a cumulative amount of product produced by the catalyst expressed as weight units of product produced per weight unit of catalyst.

Example 1

Figure 1:
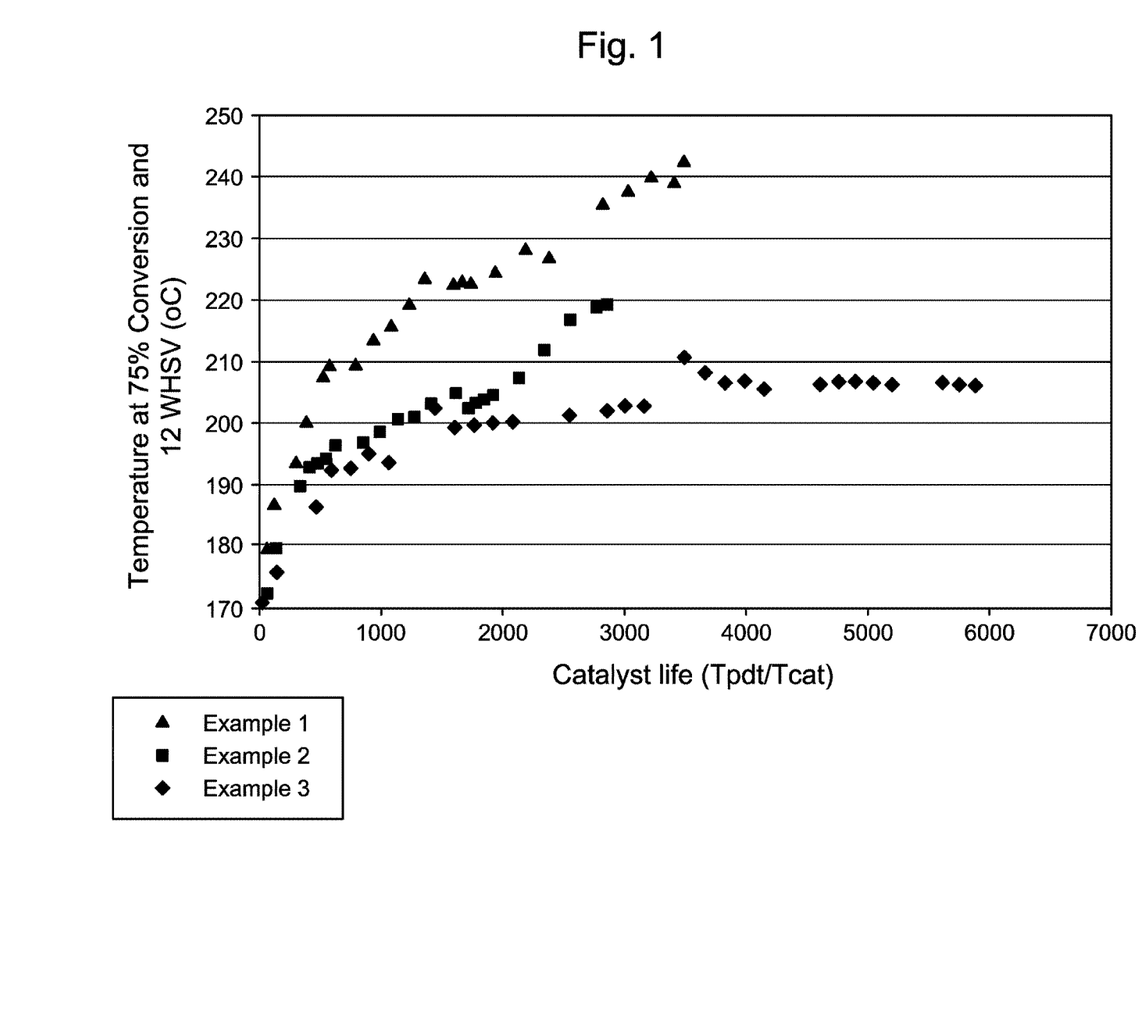
FIG. 1 is a plot at the conversion shown of the catalyst life of various examples.

ZSM-57/alumina extrudates ($\frac{1}{16}^{th}$ inch (1.5875 mm) quadrulobes) were used to to process 65 wt % n-butenes/25 wt % n-butane/10 wt % isobutane feedstock. Reaction conditions were 7000 kPa (70 bar), WHSV between 6 and 18 $hr^{-1}$, and at 170 to 240° C. feedstock inlet temperature. The temperature required to maintain 75% of olefin conversion is shown in FIG. 1 (triangles) as a function of catalyst life (weight product/weight catalyst). A catalyst life of 3000 T product/T catalyst (Tpdt/Tcat) was reached at ~240° C. $C_8$ selectivity data at 12 WHSV are plotted (triangles) in FIG. 2. At 75% conversion the $C_8$ selectivity is ~80 wt %.

Example 2

ZSM-57/alumina extrudates ($\frac{1}{20}^{th}$ inch (1.2700 mm) quadrulobes) were used to process 65 wt % n-butenes/25 wt % n-butane/10 wt % isobutane feedstock. Reaction conditions were 7000 kPa (70 bar), WHSV between 6 and 18 $hr^{-1}$, and at 170 to 220° C. feedstock inlet temperature. The temperature required to maintain 75% of olefin conversion is shown in FIG. 1 as a function of catalyst life (weight product/weight catalyst). A catalyst life of 3000 T product/T catalyst (Tpdt/Tcat) was reached at ~220° C. $C_8$ selectivity data at 12 WHSV are plotted (squares) in FIG. 2. At 75% conversion the $C_8$ selectivity is ~86 wt %.

Example 3

ZSM-57/alumina spheroids particles (sieved on ASTM 16 (mesh size)=1.2 mm) were used to process 65 wt % n-butenes/25 wt % n-butane/10 wt % isobutane feedstock. Reaction conditions were 7000 kPa (70 bar), WHSV=12 $hr^{-1}$, and at 170 to 210° C. feedstock inlet temperature. The temperature required to maintain 75% of olefin conversion is shown in FIG. 1 as a function of catalyst life (weight product/weight catalyst). A catalyst life of 3000 T product/T catalyst (Tpdt/Tcat) was reached at ~200° C. $C_8$ selectivity data at WHSV=12 $hr^{-1}$ are plotted (diamonds) in FIG. 2. At 75% conversion the $C_8$ selectivity is 88 wt %.

Example 4

Figure 3:
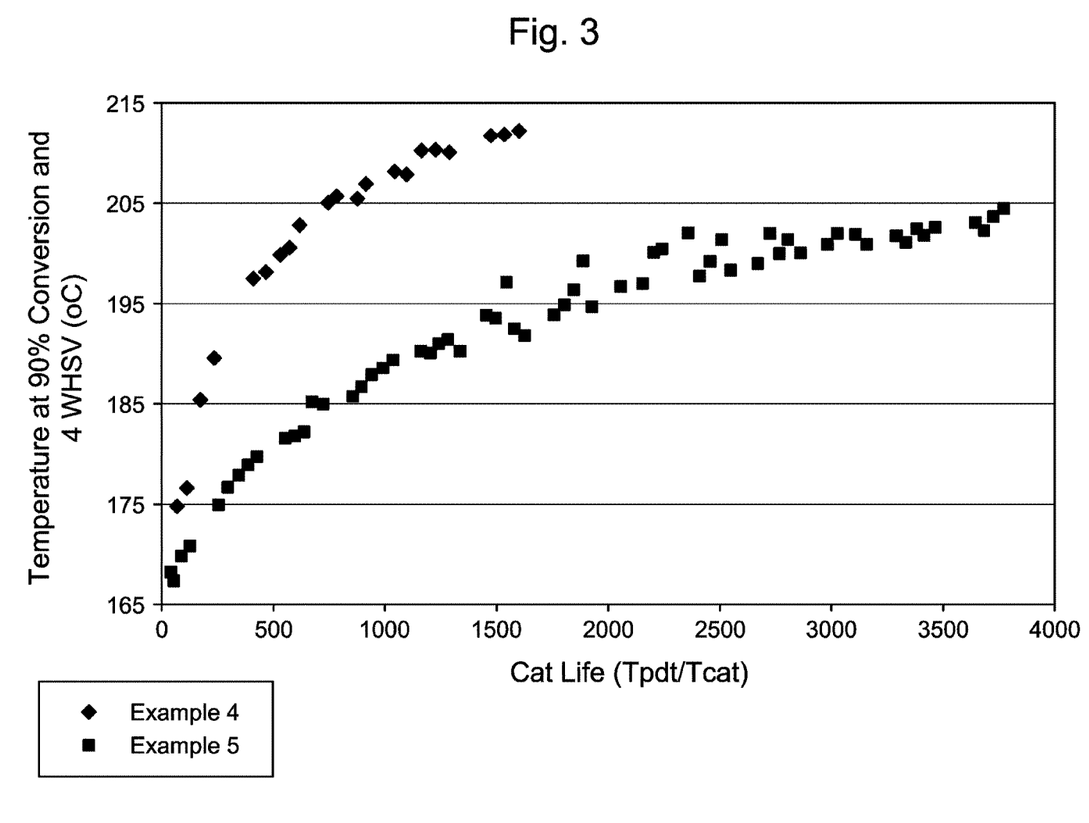
FIG. 3 is a plot at the conversion shown of the catalyst life of various examples.

ZSM-57/alumina extrudates ($\frac{1}{16}^{th}$ inch (1.5875 mm) quadrulobes) were used to process 50 wt % propylene/22.5 wt % propane/22.5 wt % n-butane/5 wt % isobutane feedstock. Reaction conditions were 7000 kPa (70 bar). WHSV between 4 and 12 $hr^{-1}$, and at 175 to 215° C. feedstock inlet temperature. The temperature required to maintain 75% of olefin conversion is shown in FIG. 3 as a function of catalyst life (weight product/weight catalyst). A catalyst life of 2000 T product/T catalyst (Tpdt/Tcat) was reached at ~215° C. $C_9$ selectivity data at WHSV=4 $hr^{-1}$ are plotted (diamonds) in FIG. 4. At 90% conversion the $C_9$ selectivity is ~60-62 wt %.

Example 5

ZSM-57/alumina spheroids particles (sieved on ASTM 16 (mesh size)=1.2 mm) were used to process 50 wt % propylene/22.5 wt % propane/22.5 wt % n-butane/5 wt % isobutane feedstock. Reaction conditions were 7000 kPa (70 bar), WHSV=4 $hr^{-1}$, and at 175 to 215° C. feedstock inlet temperature. The temperature required to maintain 75% of olefin conversion is shown in FIG. 3 as a function of catalyst life (weight product/weight catalyst). A catalyst life of 2000 T product/T catalyst (Tpdt/Tcat) was reached at ~205° C. $C_9$ selectivity data at WHSV=4 hr are plotted (squares) in FIG. 4. At 90% conversion the $C_9$ selectivity is ~66-68 wt %.

Figure 2:
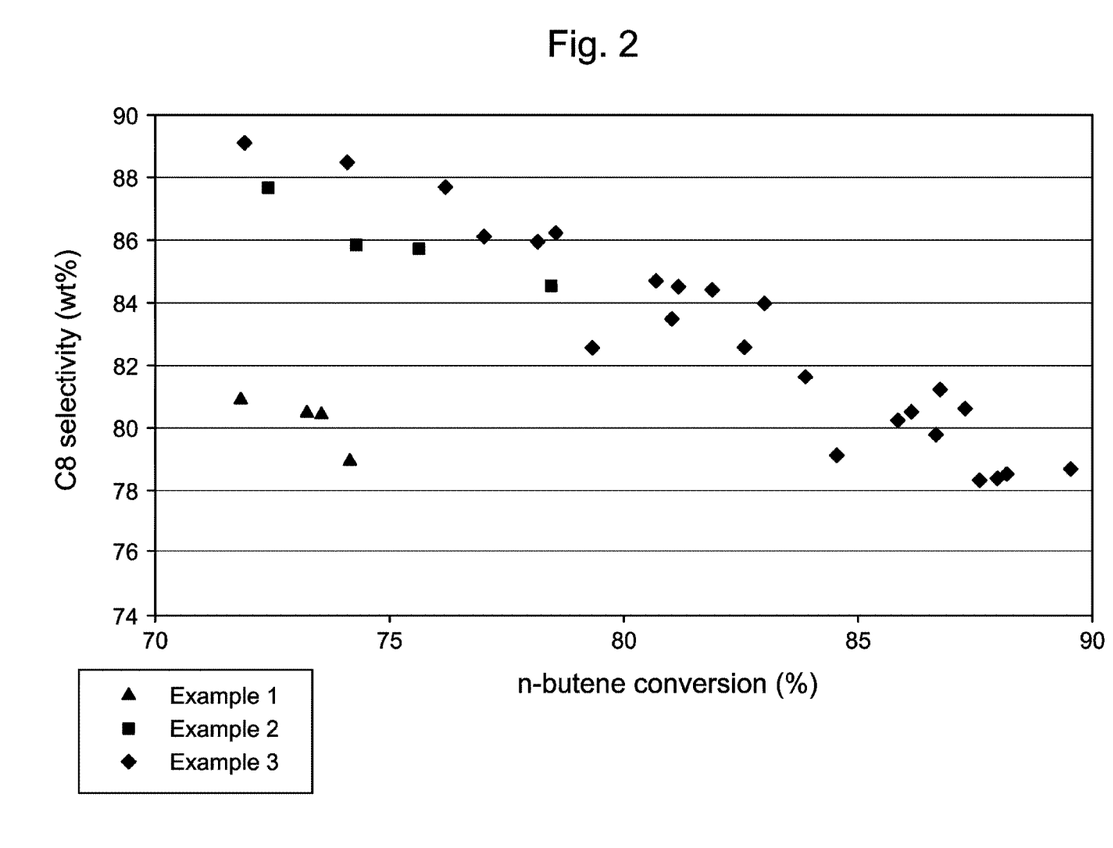
FIG. 2 is a plot showing the $C_8$ selectivity of various examples during n-butene conversion.
Figure 4:
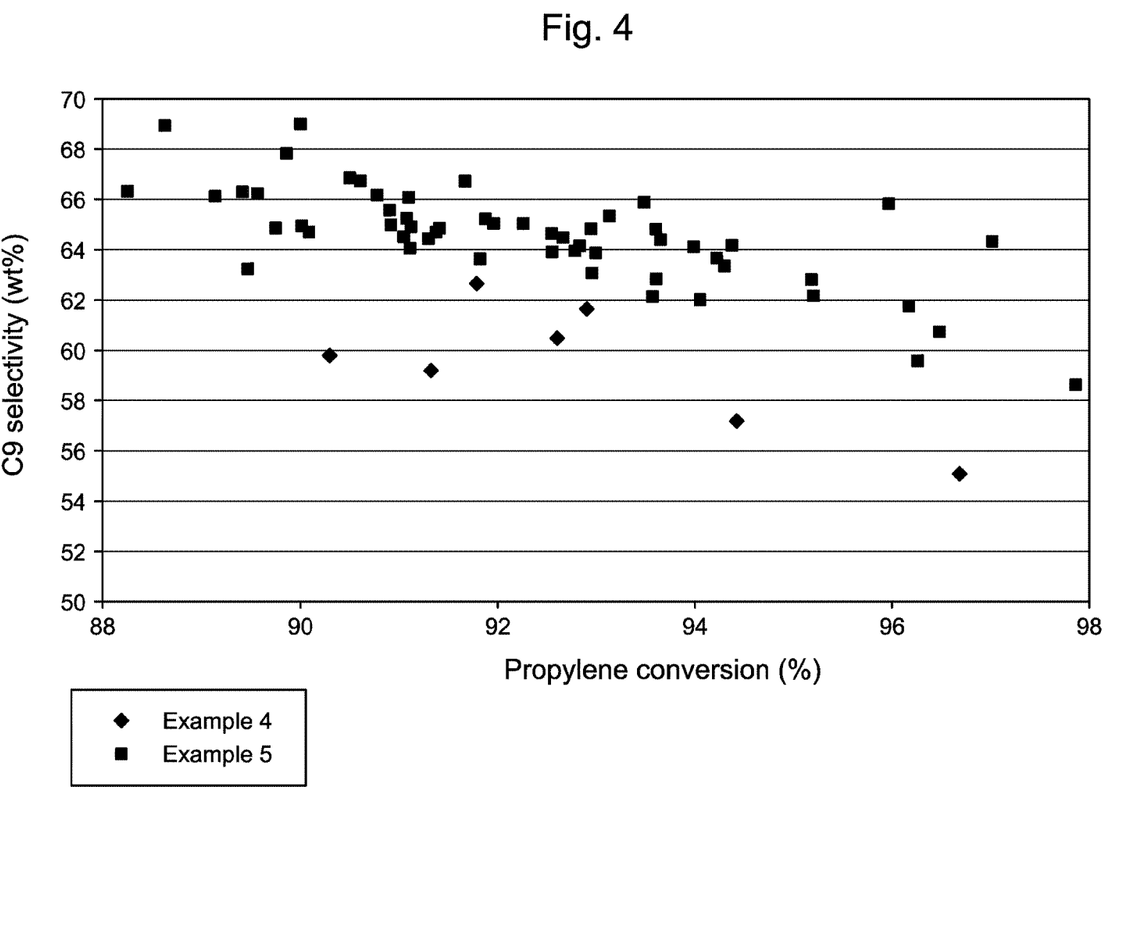
FIG. 4 is a plot showing the $C_9$ selectivity of various examples during propylene conversion.

In FIGS. 1 and 3, the weight unit chosen is "ton" (1 ton=1000 kg), denoted as T in the drawing. The longer a reactor runs at constant conditions within the practical temperature range of the unit expressed whether as days on stream or T product/T catalyst, the more stable the catalyst. Example 3 shows that the spheroid particles are much more stable in butene oligomerization than the extrudates of Examples 1 and 2. Example 5 shows that the spheroid particles are much more stable in propylene oligomerization than the extrudates of Example 4. FIG. 2 shows that the spheroid particles of Example 3 are more $C_8$ selective than the extrudates of Examples 1 and 2 at a given conversion. FIG. 4 shows that the spheroid particles of Example 5 are more $C_9$ selective than the extrudates of Example 4.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used. For example, in any of the embodiments described herein, the process may consist essentially of one or more single-step oligomerization processes. As used here, "consist essentially" would exclude the multi-step processes disclosed in U.S. Pat. No. 7,374,662.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing, procedures, publications, patents, journal articles, etc. are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A process for the oligomerization of olefins, the process comprising contacting at least one spheroid particle with a feedstock under oligomerization conditions to form at least one oligomer product,
    wherein the spheroid particle has an average particle size of from 0.1 mm to 5.0 mm and comprises the product of:
    (1) at least one zeolite catalyst which comprises TON or MFS framework structure; and
    (2) at least one binder which comprises metal oxide and/or clay,
    wherein the feedstock comprises one or more of propene, pentenes, hexenes, their isomers, and mixtures thereof.

2. The process of claim 1, wherein the feedstock comprises one or more of propane, pentane, hexane, their isomers, or a mixture thereof.

3. The process of claim 1, wherein the process comprises a catalyst life of 10% or greater as compared to an extrudate of the same chemical composition in the shape of a (1/16th inch (1.5875 mm) quadrulobe or 1/20th inch (1.2700 mm) quadrulobe); at oligomerization temperatures of from 180° C. to 320° C.; at an olefin constant per pass conversion rate of from 60 to 99 wt % based upon the total weight of olefins; and at a space velocity of from 1 to 20 $h^{-1}$.

4. The process of claim 1, wherein the process comprises a catalyst life of 30% or greater as compared to an extrudate of the same chemical composition in the shape of a (1/16th inch (1.5875 mm) quadrulobe or 1/20th inch (1.2700 mm) quadrulobe); at oligomerization temperatures of from 180° C. to 320° C.; at an olefin constant per pass conversion rate of from 60 to 99 wt % based upon the total weight of olefins; and at a space velocity of from 1 to 20 $h^{-1}$.

5. The process of claim 1, wherein the process comprises a catalyst life of 50% or greater as compared to an extrudate of the same chemical composition in the shape of a (1/16th inch (1.5875 mm) quadrulobe or 1/20th inch (1.2700 mm) quadrulobe); at oligomerization temperatures of from 180° C. to 320° C.; at an olefin constant per pass conversion rate of from 60 to 99 wt % based upon the total weight of olefins; and at a space velocity of from 1 to 20 $h^{-1}$.

6. The process of claim 1, wherein the process comprises a catalyst life of 75% or greater as compared to an extrudate of the same chemical composition in the shape of a (1/16th inch (1.5875 mm) quadrulobe or 1/20th inch (1.2700 mm) quadrulobe); at oligomerization temperatures of from 180° C. to 320° C.; at an olefin constant per pass conversion rate of from 60 to 99 wt % based upon the total weight of olefins; and at a space velocity of from 1 to 20 $h^{-1}$.

7. The process of claim 1, wherein the process comprises an olefin selectivity increase of 1 wt % or greater as compared to an extrudate of the same chemical composition in the shape of a (1/16th inch (1.5875 mm) quadrulobe or 1/20th inch (1.2700 mm) quadrulobe); at oligomerization temperatures of from 180° C. to 320° C.; at an olefin constant per pass conversion rate of from 60 to 99 wt % based upon the total weight of olefins; and at a space velocity of from 1 to 20 $h^{-1}$.

8. The process of claim 1, wherein the process comprises an olefin selectivity increase of 2 wt % or greater as compared to an extrudate of the same chemical composition in the shape of a (1/16th inch (1.5875 mm) quadrulobe or 1/20th inch (1.2700 mm) quadrulobe); at oligomerization temperatures of from 180° C. to 320° C.; at an olefin constant per pass conversion rate of from 60 to 99 wt % based upon the total weight of olefins; and at a space velocity of from 1 to 20 $h^{-1}$.

9. The process of claim 1, wherein the process comprises an olefin selectivity increase of 3 wt % or greater as compared to an extrudate of the same chemical composition in the shape of a (1/16th inch (1.5875 mm) quadrulobe or 1/20th inch (1.2700 mm) quadrulobe); at oligomerization temperatures of from 180° C. to 320° C.; at an olefin constant per pass conversion rate of from 60 to 99 wt % based upon the total weight of olefins; and at a space velocity of from 1 to 20 $h^{-1}$.

10. The process of claim 1, wherein the zeolite having TON framework in ZSM-22.

11. The process of claim 1, wherein the zeolite having MFS framework is ZSM-57.

* * * * *